(12) United States Patent
Edwards

(10) Patent No.: US 9,623,157 B2
(45) Date of Patent: Apr. 18, 2017

(54) MODIFIED HYALURONATE HYDROPHILIC COMPOSITIONS, COATINGS AND METHODS

(71) Applicant: Lake Region Manufacturing, Inc., Chaska, MN (US)

(72) Inventor: Peter Anthony Edwards, Cokato, MN (US)

(73) Assignee: Lake Region Manufacturing, Inc., Chaska, MN (US)

( * ) Notice: Subject to any disclaimer, the term of this patent is extended or adjusted under 35 U.S.C. 154(b) by 0 days.

(21) Appl. No.: 15/231,844

(22) Filed: Aug. 9, 2016

(65) Prior Publication Data
US 2016/0346439 A1 Dec. 1, 2016

Related U.S. Application Data

(63) Continuation-in-part of application No. 13/834,810, filed on Mar. 15, 2013, now abandoned.

(51) Int. Cl.
| | |
|---|---|
| C08G 59/22 | (2006.01) |
| C08L 63/00 | (2006.01) |
| A61L 31/10 | (2006.01) |
| C08B 37/08 | (2006.01) |
| C08G 18/78 | (2006.01) |
| C08G 18/58 | (2006.01) |

(Continued)

(52) U.S. Cl.
CPC ............ *A61L 31/10* (2013.01); *A61L 29/085* (2013.01); *A61L 31/14* (2013.01); *C08B 37/0072* (2013.01); *C08G 18/584* (2013.01); *C08G 18/7812* (2013.01); *C08G 59/26* (2013.01); *C08G 59/28* (2013.01); *C08G 59/32* (2013.01); *C08G 59/4215* (2013.01); *C08G 59/62* (2013.01); *C09D 163/00* (2013.01); *A61L 2400/10* (2013.01); *A61L 2420/02* (2013.01)

(58) Field of Classification Search
CPC ...... A61L 31/10; A61L 31/14; A61L 2400/10; A61L 2420/02; A61L 29/085; C08B 37/0072; C08G 18/7812; C08G 18/584; C08G 59/26; C08G 59/28; C08G 59/32; C08G 59/4215; C08G 59/62; C09D 163/00
USPC ....................................................... 523/1, 400
See application file for complete search history.

(56) References Cited

U.S. PATENT DOCUMENTS

| | | | |
|---|---|---|---|
| 4,716,224 A * | 12/1987 | Sakurai ................. | A61K 8/735 514/825 |
| 4,886,787 A | 12/1989 | de Belder et al. | |

(Continued)

FOREIGN PATENT DOCUMENTS

EP 1023090 EP 1/2003

OTHER PUBLICATIONS

International Search for PCT/US2014/027552 dated Aug. 18, 2014.
Endre A. Balazs, "Physical Chemistry of Hyaluronic Acid", Federation Proceedings, vol. 17, 1958, 1086-1093.
Edwards et al., "Novel Polyurethane Coating Technology Through Glycidyl Carbamate Chemistry", Journal of Coatings Technology Research; vol. 2, No. 7, Jul. 2005, 517-527.

(Continued)

*Primary Examiner* — David Karst
(74) *Attorney, Agent, or Firm* — Michael F. Scalise

(57) ABSTRACT

This invention relates to hydrophilic polymer compositions and a preferred application therefore, viz., hydrophilic medical device coatings. The hyaluronic acid hyaluronon by itself or modified as described herein advantageously reacts with compositions disclosed in U.S. Pat. No. 7,776,956 to produce hydrophilic compositions and coatings particularly useable with medical devices.

28 Claims, 4 Drawing Sheets

(51) Int. Cl.
| | |
|---|---|
| A61L 31/14 | (2006.01) |
| A61L 29/08 | (2006.01) |
| C08G 59/26 | (2006.01) |
| C08G 59/28 | (2006.01) |
| C08G 59/32 | (2006.01) |
| C08G 59/42 | (2006.01) |
| C08G 59/62 | (2006.01) |
| C09D 163/00 | (2006.01) |

(56) References Cited

U.S. PATENT DOCUMENTS

| | | | |
|---|---|---|---|
| 5,789,571 A * | 8/1998 | Beavers | C07H 7/033 |
| | | | 536/119 |
| 6,042,876 A | 3/2000 | Deem et al. | |
| 6,673,453 B2 | 1/2004 | Beavers et al. | |
| 7,776,956 B2 | 8/2010 | Webster et al. | |
| 2006/0153893 A1 | 7/2006 | Matsuno et al. | |
| 2010/0189758 A1 | 7/2010 | Kleiner et al. | |
| 2010/0216951 A1 | 8/2010 | Webster et al. | |
| 2012/0041554 A1 | 2/2012 | Hu et al. | |
| 2012/0316329 A1* | 12/2012 | Fujikawa | A61K 8/345 |
| | | | 536/53 |
| 2013/0317286 A1 | 11/2013 | Bluecher et al. | |
| 2015/0183891 A1 | 7/2015 | Gianmmona et al. | |

OTHER PUBLICATIONS

Edwards et al., "Synthesis, characterization and self-crosslinking of glycidyl carbamate functional resins", Progress in Organic Coatings, An International Journal, 2006, 128-139.
Harkal et al., "Linear glycidyl carbamate (GC) resins for highly flexible coatings", J. Coat Technol. Res.; 11 pages, Aug. 1, 2012.
Laurent et al., "Fractionation of Hyaluronic Acid The Polydispersity of Hyaluronic Acid from the Bovine Vitreous Body", Biochimica et Biophysica Acta; vol. 42, Jan. 4, 1960, 476-485.
Lee et al., "Multiple Voltammetric Peaks of the First Redox Process of Self-assembled N-Docosyl-N-Methyl Viologen(2+) Molecular Films at Elecreode Surfaces", Bull. Korean Chem. Soc. vol. 15. No. 3, 1994, 3 pages.
Karl Meyer, "Chemical Structure of Hyaluronic Acid", Federation Proceedings; vol. 17, 1958, 1075-1077.
Meyer et al., "On Glycoproteins II. The Polysaccharides of Vitreos Humor and of Umbilical Cord", Apr. 3, 1936, 689-703.
Meyer et al., "The Polysaccharide of the Vitreous Humor", Sep. 4, 1934, 629-634.
Necas et al., "Hyaluronic acid (hyaluronan): a review", Veterinami Medicina, 53, 2008 (8):., 397-411.
Weissmann et al., "The Structure of Hyalobiuronic Acid and of Hyaluronic Acid from Umbilical Cord", The Journal of the American Chemical Society; vol. LXXVI, 1954, 1753-1757.

* cited by examiner

MODIFIED HYALURONATE HYDROPHILIC COMPOSITIONS, COATINGS AND METHODS

CROSS-REFERENCE TO RELATED APPLICATION

This application is a continuation-in-part of U.S. patent application Ser. No. 13/834,810, filed on Mar. 15, 2013, abandoned.

BACKGROUND OF THE INVENTION

This invention relates to hydrophilic polymer compositions and a preferred application therefore, viz., hydrophilic medical device coatings.

Glycosaminoglycans, specifically including but not limited to hyaluronic acid ("HA") (also referred to as hyaluronan or hyaluronate) modified according to this invention provide a biocompatible, highly lubricious, durable, hydrophilic coating material. When used with, or crosslinked to, an optional base coat, the HA-based hydrophilic coatings of this invention can be applied to both metal and polymer substrates. Acutely-used i.e., intravascularly deployed for about 30 days or less, medical devices, e.g., catheters and guidewires, constitute a particularly preferred coating application for compositions of this invention.

THE PRIOR ART

Hyaluronic acid, hyaluronate, hyaluronon, (including salts thereof) hereafter collectively "HA" is a naturally occurring high viscosity glycosaminoglycan having alternating β1-3 glucuronidic and β1-4 glucosaminidic bonds. The molecular weight of HA is generally within the range of <10,000 to 8,000,000 depending on the source, method of isolation and method of determination (Lifecore Biomedical web site). It is found in animal tissue, e.g., in umbilical cord, vitreous humor, synovial fluid, rooster combs, pathologic joints, group A and C hemolytic streptococci and in skin.

The isolation and characterization of HA is described in Meyer et al., J. Biol. Chem. 107, 629 (1934); J. Biol. Chem. 114, 689 (1936); Balazs, Fed. Proc. 17, 1086 (1958); Laurent et al.; Biochem. Biophys. Acta 42, 476 (1960). The structure of HA was elucidated by Weissman et al. J. Am. Chem. Soc. 76, 1753 (1954) and Meyer, Fed. Proc. 17, 1057 (1958). Cf., U.S. Pat. No. 4,141,973 Balazs, incorporated by reference herein. A representative structure of HA is shown in the Figures.

The application of unmodified HA to guidewires is noted in U.S. Pat. No. 6,042,876 to Deem, the teaching of which is incorporated by reference herein.

Belder and Malson et al. in U.S. Pat. No. 4,886,787 disclose Under alkaline conditions, ether linkages are generated from the di-epoxide hyaluronan reaction with hydroxyl functionality, while acid conditions form an ester.

Agerup in U.S. Pat. No. 4,886,787 discloses a process where HA is crosslinked with a di-epoxide.

The self-crosslinking reaction and oligomers of glycidyl carbamate ("GC") is described by Edwards et al. in Prog. Org. Coat., 57, 128-139 (2006).

Edwards et al. in JCT Research, 2(7), 517-528 (2005) describes reactions of glycidyl carbamate with various amines.

HYDAK A-16, is a coating composition available from Biocoat, Inc. is disclosed to comprise hyaluronic acid, polyacrylic acid and adjuvants, Cf., U.S. Pat. No. 6,673,453 to Beavers et al., col. 11, line 54, which is incorporated by reference herein. It is further noted in the '453 patent that free-acid form hyaluronic acid is obtainable from Biocoat, Inc. (col. 15, line 29).

Webster et al. in U.S. Pat. No. 7,776,956 (hereafter "the '956 patent") disclose water-dispersible epoxy urethane compounds and coating compositions. The disclosure of the '956 patent is specifically incorporated by reference herein in its entirety. The '956 patent discloses compositions comprising a polyfunctional oligomer having at least two epoxy urethane functional groups and a hydroxylated polyalkylene oxide chain. The compositions can be dispersed in water, with optionally added surfactants, to form a dispersion which is substantially free of volatile organic solvents.

No mention is made in the '956 patent of the possible use of the compositions of the patent to modify other polymers.

BRIEF SUMMARY OF THE INVENTION

The present composition is particularly advantageously used as a top coat material on medical devices such as catheters, guidewires, or sheaths. The coating is advantageously hydrophilic, non-thrombogenic, lubricious and durable.

In its several aspects, the present composition is:
a. HA fully or partially reacted with compositions of the noted '956 patent.
b. A coating composition of HA fully or partially reacted with compositions of the noted '956 patent that further comprises the self-crosslinking the '956 patent moiety.
c. HA reacted with an isocyanate modified with mPEG end-capped and glycidol end capped isocyanate mixed pre-polymer of the noted '956 patent.

In a further aspect, the present invention is HA modified as noted in the previous paragraph, deployed as a coating, which further includes a base coat interposed between the modified HA top coat and the exterior of the structure on which the coating is applied.

BRIEF DESCRIPTION OF THE FIGS.

DETAILED DESCRIPTION OF THE INVENTION

Figure 1:
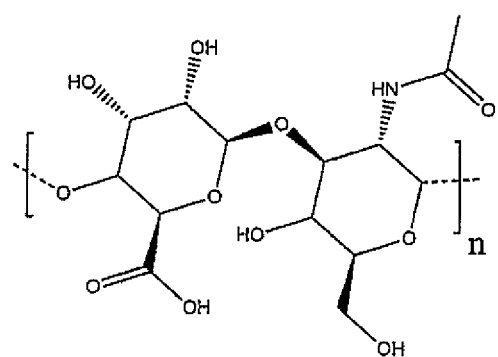
FIG. 1 shows the structural formula of "hyaluronic acid" (HA)

HA, for purposes of this invention, has a structural formula as shown in FIG. 1. As is noted above, the molecular weight of HA is in the range of <10,000 to as great as 8,000,000, or greater, meaning that "n" in this structural formula of FIG. 1 generally falls in the range of about <25 to about 25,000 or greater. It is to be understood that for purposes of this application the abbreviation "HA" is to be broadly construed to mean hyaluronic acid free and salts thereof, and hyaluronon or hyaluronate, and any of their commonly interchanged terms, which collectively refer to or references easily chemically interchanged species such as salts, esters, amides, acid halides and so forth. Generally speaking HA, as used herein, will have the structure shown in FIG. 1 and will have a structural formula of $(C_{14}H_{21}NO_{11})_n$.

In a first embodiment of this invention, HA, broadly construed, is partially or fully reacted with a composition of the '956 patent. The details of the chemistry of the '956 patent applicable to reaction with HA in accordance with this invention are set forth below.

In a further embodiment, a composition as described in the above paragraph is further reacted e.g., by heating, to induce self-crosslinking of a '956 patent moiety with a second '956 patent moiety.

Figure 2A:
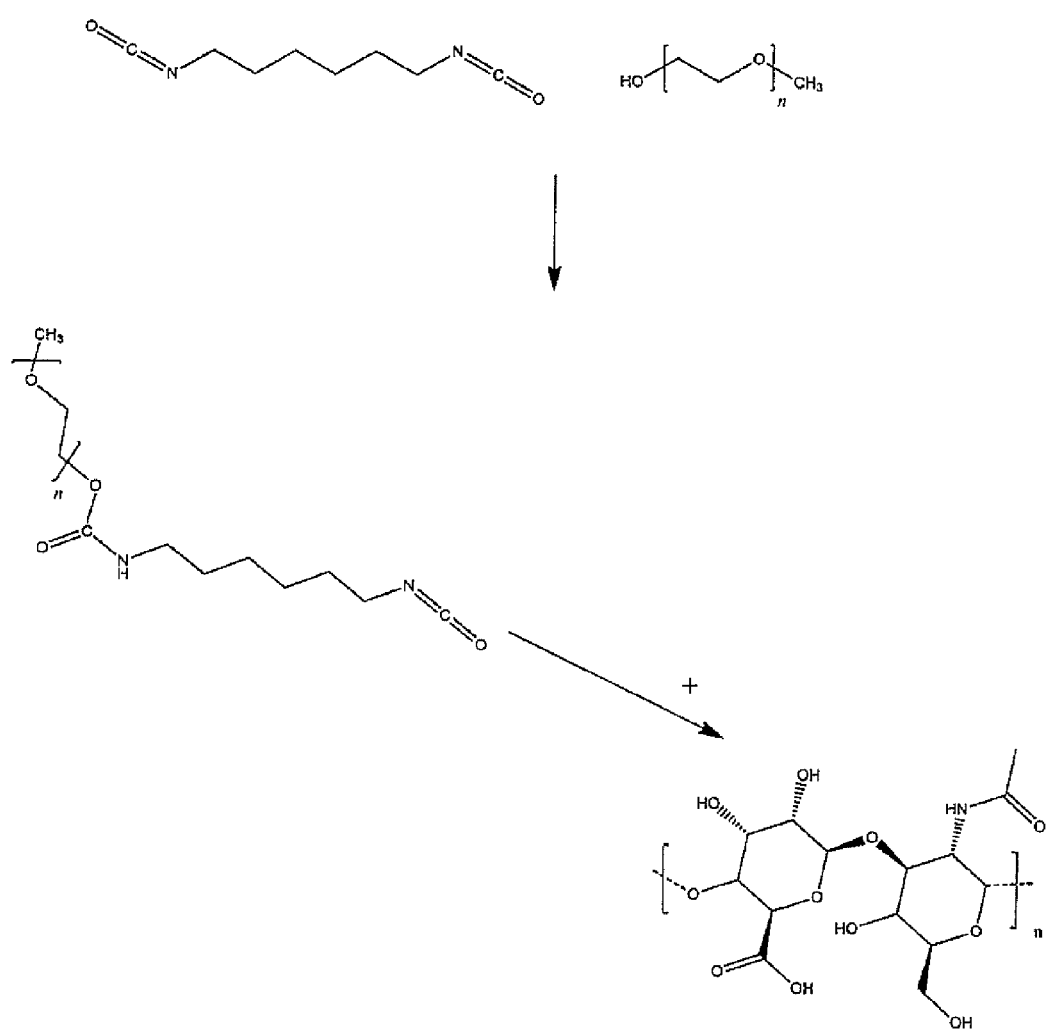
FIGS. 2A and 2B show a general synthetic route for a composition of this invention.
Figure 2B:
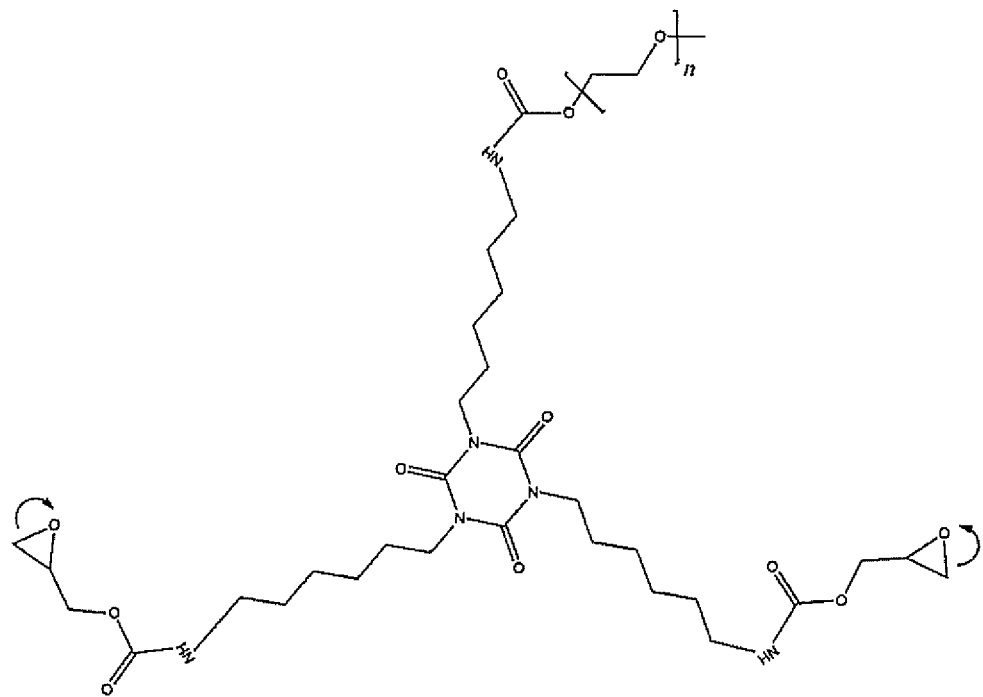

In yet a further embodiment HA, broadly construed, is reacted with an isocyanate, also broadly construed, which is mPEG end-capped, the reaction product being reacted with a composition of the '956 patent (FIGS. 2A, 2B) (synthetic details below).

According to this invention, HA, broadly construed, is modified by reacting it with an isocyanate prepolymer, or precursor which is a di- or poly-isocyanate, the di- or poly-isocyanate being end-capped with a segment, moiety or chain of methoxy poly (ethylene glycol), in abbreviated form referenced as "mPEG". mPEG has the structural formula of:

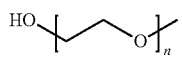

where "n" has a value of about 5 to 50, preferably about 12.5 to 42. It is to be understood that mPEG is a representative preferred example of the alkoxy polyalkylene glycol family of polymers.

Using a representative diisocyanate, e.g., hexamethylene diisocyanate, an isocyanate end-capped pre-polymer with mPEG has the formula:

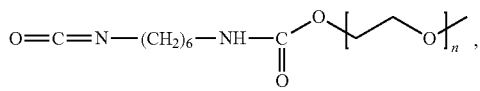

"n" having the values noted above.

Using a representative diisocyanate, e.g., hexamethylene diisocyanate, an isocyanate end-capped pre-polymer with glycidol has the formula:

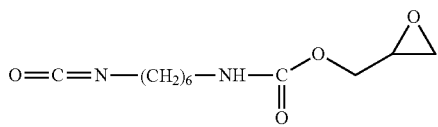

The above mPEG end-capped and glycidol end capped isocyanate mixed pre-polymer then is reacted with HA, noted above, to produce what is referenced here as "mPEG-NCO modified HA" according to this invention as follows:

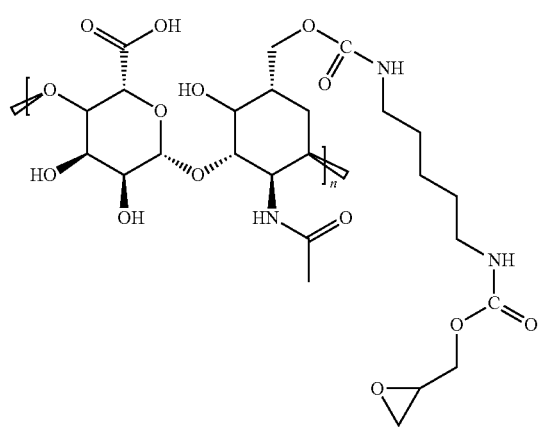

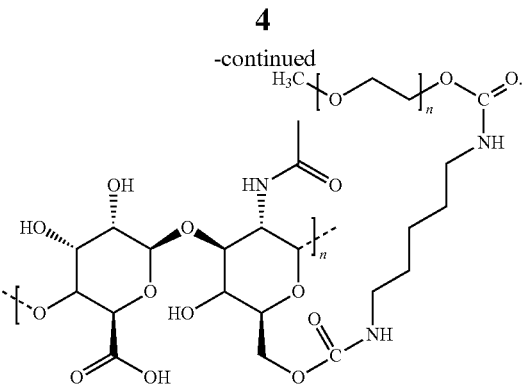

Mpeg and GC are mono-functional. GC is difficult to mix in alone, and thus requires a blend.

Figure 3:
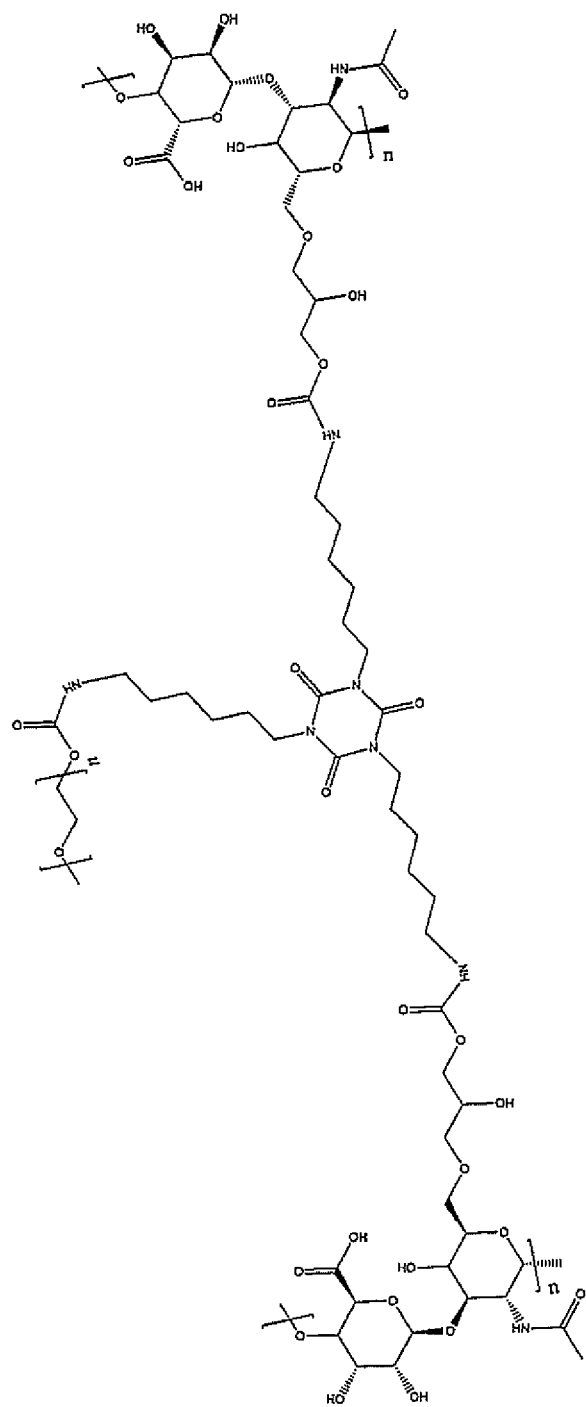
FIG. 3 shows a likely structure of a modified HA material of this invention.

The oligomer of the '956 patent is fully reacted with HA, noted above, to produce what is referenced here as "'956 patent modified or partially modified HA" according to this invention. Partially modified HA can then be reacted further with HA or with externally added crosslinkers. The structural formula below (and FIG. 3) shows a likely structure of a modified HA material of this invention.

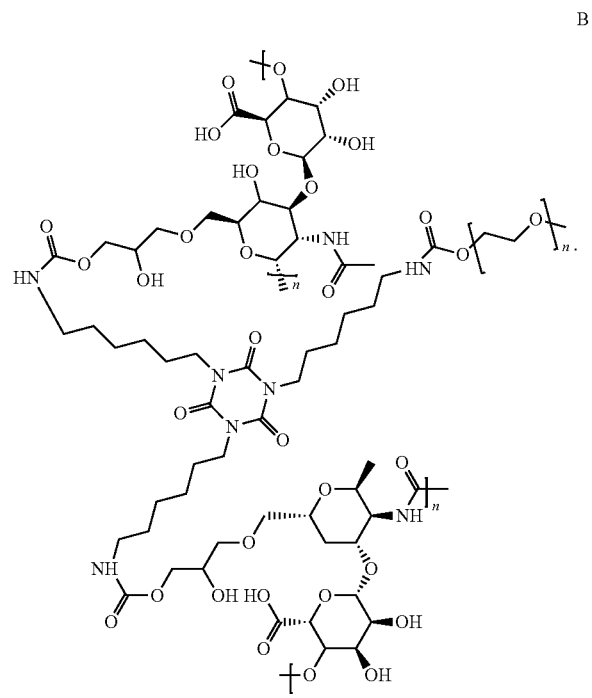

Without wishing to be bound by any theory it is theorized that the alcohol of Hyaluronan may help promote polyetherification or crosslink the Hyaluronan system.

The oligomer of the '956 patent is partially reacted with HA, noted above, to initiate the self-crosslinking reaction (temperatures >75 C) to produce what is referenced here as "partially modified HA" according to this invention. The sequence below shows a likely structure of a modified HA material of this invention. During the modification of HA the polyurethane epoxy may undergo etherification or homopolymerization. This reaction may be initiated or involve Hyaluronan or self-crosslink of the GC moiety.

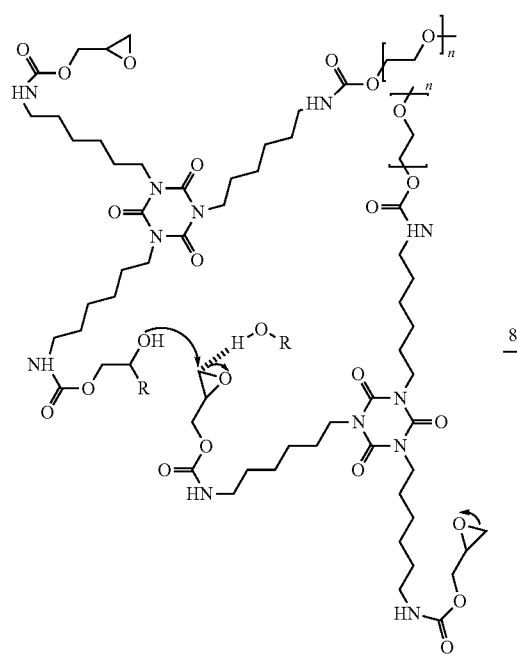

R = Neucleophile

ETHERIFICATION

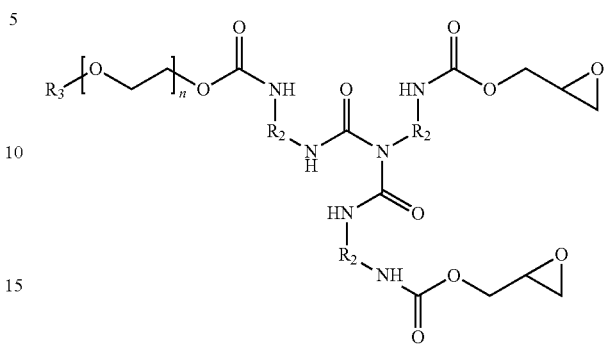

Oligomers of the '956 Patent

The '956 patent discloses compositions comprising a polyfunctional oligomer having at least two epoxy urethane functional groups and a hydroxylated polyalkylene oxide chain. The compositions can be dispersed in water, with optionally added surfactants, to form a dispersion containing no volatile organic solvents.

The '956 patent discloses water-dispersible epoxy urethane resins of the Formula (I) or Formula (II).

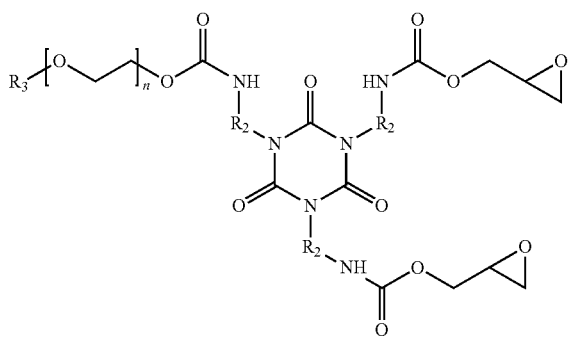

(I)

or

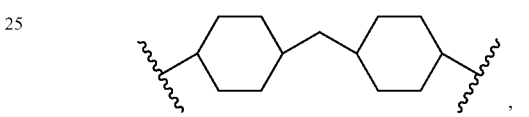

(II)

wherein $R_2$ is independently an optionally substituted, divalent $C_1$-$C_{15}$ alkyl, optionally substituted divalent $C_3$-$C_{15}$ cycloalkyl, or a group selected from

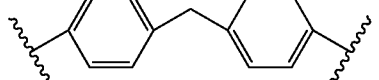

,

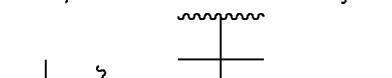

,

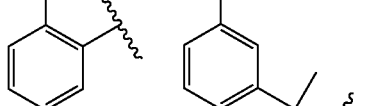

,

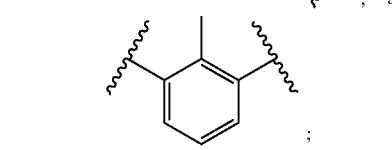

, and

,

;

and $R_3$ is independently an optionally substituted $C_1$-$C_{15}$ alkyl or an optionally substituted divalent $C_3$-$C_{10}$ cycloalkyl.

In a preferred practice of the present invention, n=1, $R_2$=(—$CH_2$—)$_6$, and $R_3$=$CH_3$— is used.

Polyfunctional oligomers of the '956 patent are prepared from the reaction of hydrophilic modified polyfunctional resin having the disfunctional isocyanates with glycidol. The polyfunctional resin is derived from controlled polymerization or oligomerization of the difunctional isocyanates. Free isocyanate is reacted with glycidol to form an epoxy urethane functional resin. The polyfunctional resin also includes a polyfunctional biuret.

Any suitable organic di-, tri-, or polyisocyanate, such as an aliphatic, cycloaliphatic, araliphatic or aromatic polyisocyanate, may be used either singly or in mixtures of two or more. The aliphatic isocyanates provide generally better light stability than the aromatic compounds. Aromatic polyisocyanates, on the other hand, are generally more economical and reactive toward polyols and other poly(active hydrogen) compounds than aliphatic polyisocyanates. Suitable aromatic polyisocyanates include but are not limited to those selected from the group consisting of 2,4-toluene diisocyanate, 2,6-toluene diisocyanate, a dimer of toluene diisocyanate (available under the Desmodur™ trademark from Bayer Materials Science, Leverkusen, Germany), diphenylmethane 4,4'-diisocyanate (MDI), 1,5-diisocyanato-naphthalene, 1,4-phenylene diisocyanate, 1,3-phenylene diisocyanate, fluorinated and/or silicone containing derivatives of the aforementioned, and mixtures thereof. Examples of useful cycloaliphatic polyisocyanates include but are not limited to those selected from the group consisting of dicyclohexylmethane diisocyanate ($H_{12}$ MDI, commercially available under the Desmodur™ trademark from Bayer Materials Science, Leverkusen, Germany), isophorone diisocyanate (IPDI), 1,4-cyclohexane diisocyanate (CHDI), 1,4-cyclohexanebis(methylene isocyanate) (BDI), 1,3-bis(isocyanatomethyl)cyclohexane ($H_6$XDI), and mixtures thereof. Examples of useful aliphatic polyisocyanates include but are not limited to those selected from the group consisting of hexamethylene 1,6-diisocyanate (HDI), 1,12-dodecane diisocyanate, 2,2,4-trimethyl-hexamethylene diisocyanate (TMDI), 2,4,4-trimethyl-hexamethylene diisocyanate (TMDI), 2-methyl-1,5-pentamethylene diisocyanate, dimer diisocyanate, the urea of hexamethyl diisocyanate, and mixtures thereof. Examples of useful araliphatic polyisocyanates include but are not limited to those selected from the group consisting of m-tetramethyl xylylene diisocyanate (m-TMXDI), p-tetramethyl xylylene diisocyanate (p-TMXDI), 1,4-xylylene diisocyanate (XDI), 1,3-xylylene diisocyanate, or mixtures thereof.

Preferably, the polyfunctional resin derived from isocyanate or biuret is selected from the group consisting of TDI (toluene diisocyanate), TDI biuret, MDI (diphenylmethane diisocyanate), MDI biuret, HDI (hexamethylene diisocyanate), HDI biuret, NDI (naphthalene diisocyanate), NDI biuret, HMDI (hydrogenated MDI), HMDI biuret, and IPDI (isophorone diisocyanate) and IPDI biuret. More preferably, a polyfunctional resin derived from isocyanate or biuret consists of HDI (hexamethylene diisocyanate) or HDI biuret.

The polyfunctional oligomer of the invention is hydrophilic. Applicable hydrophilic functionality with suitable functional groups can readily be provided with the skilled person. Preferably, the polyfunctional oligomer has a polyalkylene oxide chain with 1 to 50 alkylene oxide units, preferably 2 to 20 alkylene oxide units. More preferably, the polyalkylene oxide chain may be an ethylene oxide chain, a propylene oxide chain, or an ethylene propylene oxide chain.

A preferred polyfunctional isocyanate resin based on hexamethylene diisocyanate and having ethylene oxide units is commercially available and sold under the Bayhydur XP 7165 tradename by Bayer Materials Science, Leverkusen, Germany.

The term "alkyl" includes straight and branched alkyl groups. The term "cycloalkyl", as used herein, refers to groups having three to ten, preferably three to seven carbon atoms. Suitable cycloalkyls include, but are not limited to cyclopropyl, cyclobutyl, cyclopentyl, cyclohexyl, cycloheptyl and the like. As indicated above, $R_2$ and $R_3$ may be substituted with any number of substituents or functional moieties. Examples of substituents include, but are not limited to, halo substituents, e.g. F; Cl; Br; or I; a hydroxyl group; a $C_1$-$C_6$ alkoxy group, e.g, —$OCH_3$, —$OCH_2CH_3$, or —$OCH(CH_3)_2$; a $C_1$-$C_6$ haloalkyl group, e.g., —$CF_3$; —$CH_2CF_3$; or —$CHCl_2$; $C_1$-$C_6$ alkylthio; amino; mono and dialkyl amino groups; —$NO_2$; —CN; a sulfate group, and the like.

Optional surfactants are commonly used in coating formulations to improve wetting of the substrate by the coating, and wetting of the pigment by the resin. They can also improve formulating latitude by preventing shocking of the coating composition as various components are added and can increase the service life of the coating by increasing shelf stability. Typically, low levels of surfactants are used to accomplish these goals and mixtures of surfactants may be employed to impart one or more of the properties listed above. Surfactants are not generally volatile materials under ambient conditions and remain in the coating during the drying process. However, at the low concentrations typically used, little effect on polymer hardness or coating performance is observed. If too much surfactant is used in the aqueous coating composition, the wet coating could exhibit excessive foaming and poor thickening efficiency with thickeners while the cured coating could have problems with water sensitivity, poor exterior durability and poor block, stain and print resistance. Thus, surfactants are typically used in the lowest amounts necessary to achieve their beneficial properties while avoiding any detrimental effects.

Any anionic or nonionic surfactant, as well as mixtures, may be used in a water-based polymer coating composition of the invention. The surfactant is present in an amount effective to stabilize a coating formed from the composition. Preferably the nonionic surfactant is a polyether nonionic surfactant, more preferably, an alkyl polyglycol ether, an alkyl phenol polyglycol ether or a mixture thereof. Preferred alkyl phenol polyglycol ethers include ethoxylation products of octylphenol, nonylphenol, diisopropyl phenol, triisopropyl phenol or mixtures thereof. Preferred alkyl polyglycol ethers include ethoxylation products of lauryl alcohol, oleyl alcohol, stearyl alcohol or mixtures thereof. Preferred anionic surfactants include alkali metal or ammonium salts of alkyl, aryl or alkylaryl sulfonates, sulfates, phosphates. More preferably, the anionic surfactant is selected from sodium lauryl sulfate, sodium octylphenol glycolether sulfate, sodium dodecylbenzene sulfonate, sodium lauryldiglycol sulfate, ammonium tritertiarybutyl phenol and penta- and octa-glycol sulfonates, sulfosuccinate salts such as disodium ethoxylated nonylphenol half ester of sulfosuccinic acid, disodium n-octyldecyl sulfosuccinate, sodium dioctyl sulfosuccinate, and mixtures thereof. AEROSOL 18 surfactant, a 35% solution of disodium N-octyldecyl sulfosuccinimate in water and AEROSOL OT-75 surfactant, a 75% solution of sodium dioctyl sulfosuccinate in water, both available from Cytec Industries, Inc. are preferred anionic surfactants. Triton GR-7M is also preferred sulfosuccinate surfactant.

The HA-based coatings of the present invention can be coated upon bare metal substrates, i.e., metal surfaces of e.g., a medical devise. While not necessarily a preferred use of the compositions/coatings of this invention, application to bare metal are contemplated Generally, it is preferable to use some type of adhesion promoter on the metal itself. An adhesion promoter is generally much thinner than what is intended by the term "Base Coat" herein. Preferred adhesion promoters includes the triexthoxysilanes available from Gelest, Inc.

Base Coat (Optional)

Materials of this invention optionally may be applied over and reacted with (i.e., cross-linked to the) base coat materials of concurrently filed and incorporated by reference herein application entitled "Oxirane Polyurethane Coatings," U.S. patent application Ser. No. 13/834,988, filed on Mar. 15, 2013, now U.S. Pat. No. 9,255,173.

EXAMPLE 1

Procedure for Representative Synthesis of mPEG-NCO Modified HA
1.1 Heat all reaction flasks and tops used for all reaction(s) at 100° C. overnight to remove moisture.
1.2 Charge 1 mole, 162 grams hexamethylene dusocyanate (HDI), Sigma-Aldrich to a 50 mL cylindrical reaction vessel fitted into the appropriate heating mantel with a dry nitrogen purge.
1.4 Add ¼ mole, 187.5 grams Methoxy (polyethylene glycol), Sigma-Aldrich, 750 Mn.
1.5 Let react for 10 minutes.
1.6 Next add ¼ mole, 18.5 grams Glycidol carbamate, Dixie-Chemicals.
1.7 Mix this resin solution thoroughly at 500 RPM for 1 hr. and 30 min.
1.8 After 1 hour 30 min add 1 glass pipette drop of C-95%.
1.9 After 2 hours increase the temperature of the J-KEM to 65 C.
1.10 Hold reactor temperature, using the J-KEM and adjust with mixer RPM's to hold 80 C for 1 hour for an NCO-mpeg and NCO-GC mixture.

Modification Procedure of mPEG-NCO Modified HA
2.1 Add NCO-mpeg and NCO-GC mixture (0.500±010 g) from previous step to a 4 ounce jar and record amount.
2.2 Next add HA, Shandong Topscience Biotech Co., Ltd (3.0±050 g) MW≥2 million Injection Grade, to the 4 ounce bottle and record amount.
2.3 Mix 4 ounce bottle contents at 500 RPM for 10 minutes to fully incorporate.
2.4 Move bottle side to side for full incorporation and to fully incorporate.
2.5 Place uncapped 4 ounce bottle into the oven set at 80 C.
2.6 Heat at 80 C for 2 hours for reaction to yield the mPEG-NCO modified HA component.

EXAMPLE 2

Procedure for Representative Synthesis of '956 Modified HA
1.1 Synthesis as used in the '956 patent or materials purchased from Dixie-Chemicals as follows:

The following abbreviations and terms are used in the below:
HDI: hexamethylene diisocyanate
PACM: para amino-cyclohexyl methane
Anquamine 419: curing agent
MEK: Methyl ethyl ketone
ASTM: American Society for Testing and Materials Materials Glycidol was supplied by Dixie Chemical and stored refrigerated to minimize formation of impurities. An isocyanurate timer of HDI (hexamethylene diisocyanate) with polyethylene oxide (Bayhydur XP 7165) was used as the polyfunctional isocyanate resin with an isocyanate equivalent weight of 230. K-KAT® XC-6212 was supplied by King Industries. Triton™GR-7M anionic surfactant was provided by Union Carbide and BYK 028 defoamer was provided by BYK Chemie USA. Amines used as hardeners were purchased from Aldrich and provided by Air Products. These include; bis(para-aminocyclohexyl) methane (PACM) and Anquamine 419, respectively. D.E.R® 332 (DGEBA) was supplied by The Dow Chemical Company.

Synthesis of the Epoxy Urethane Resin

A 1000 ml four neck round bottom flask with condenser, nitrogen inlet and Model 210 J-KEM temperature controller, mechanical stirrer, with heating mantle were used for synthesis. The reaction vessel was charged with 225.21 grams glycidol and 700 grams of Bayhydur XP 7165 polyfunctional isocyanate resin and 0.112 grams K-KAT® XC-6212 (0.0025 weight percent). The temperature was held at 60° C. and the reaction was monitored and controlled within +/−two degrees Celsius. Infrared analysis was performed to determine reaction completion by monitoring the disappearance of the isocyanate peak at 2270 cm$^{-1}$. Epoxy equivalent weights were determined by titration with HBr (ASTM D1652). The theoretical epoxide equivalent weight of the product was 304, which compares with 303 grains/equivalent determined by titration.

Infrared (FTIR) measurements were performed using a Nicolet Magna-850 FTIR spectrometer. Sample aliquots were taken and coated directly on a potassium bromide salt plate. Omnic FTIR software for Nicolet was used to perform transmission with a final format of absorbance. Spectra acquisitions were based on 64 scans, resolution 4 and a data spacing of 1.98 cm.sup.−1. The main compartment was used and set for auto gain to monitor a spectral range of 4000 cm$^{-1}$ to 400 cm$^{-1}$. Different intervals of the reaction were sampled to monitor disappearance of the isocyanate peak. GRAMS 32 v5 FTIR software was employed for spectral calculations.

Aqueous Coating Compositions

Aqueous coating compositions of the invention were formulated using the epoxy urethane resin of Example 1, an amine curing agent and water without addition of organic co-solvent. Coatings were formulated using 70% epoxy urethane resin and 30% water without addition of co-solvent. After mixing the resin and water, 1-drop Triton GR-7M surfactant was added for dispersion and diluting ⅙ of a drop of BYK 028 Was used as a flow aid. Formulations were mixed with a glass stir rod, by hand, at room temperature. After the resin was dispersed in water, the amine curing agent, PACM or Anquamine 419, was added. Table 1 illustrates the formulation with actual amounts used. Coatings of from the aqueous coating compositions of the invention were prepared and tested as described below.

TABLE 1

Aqueous Coating Composition Formulation

| Formulation | Water (g) | Resin (g) | PACM (g) | Anquamine 419 (g) | Solids (%) |
|---|---|---|---|---|---|
| 1 | 3.752 | 8.474 | 1.450 | — | 69.3 |
| 2 | 4.50 | 3.752 | — | 9.710 | 69.7 |

Modification Procedure of '956 Patent Modified HA
2.1 Add '956 patent material above (0.002153 grams) to a 4 ounce jar and record amount.
2.2 Next add HA Supplier B (3.0±050 g) [MW≥2 million] [Injection Grade], to the 4 ounce bottle and record amount.
2.3 Mix 4 ounce bottle contents at 500 RPM for 10 minutes to fully incorporate.
2.4 Move bottle side to side for full incorporation and to fully incorporate.
2.5 Place uncapped 4 ounce bottle into the oven set at 80 C.
2.6 Heat at 80° C. for 2 hours for reaction to yield the '956 modified HA component.

EXAMPLE 3

A guidewire coated with un-modified Hyaluronan is difficult to insert and withdrawal in a catheter. Modification, using Mpeg isocyanate and GC isocyanate, allows for a substantial drop in lubricity, which allows the catheter to guide easily. Without modification the guidewire cannot be inserted into the catheter without force. All coatings (Modified and Un-modified), shown in the paragraph below, contain '956 patent cross-linker where ARM was optional. In all cases, modification with Mpeg isocyanate and GC isocyanate, yields a very lubricious coating.

Self-crosslinking reaction

During the modification of HA the polyurethane epoxy undergoes etherification or homopolymerization.

This reaction may be initiated or involve Hyaluronan or self-crosslink by itself.

Table of Modified Hyaluronan with Mpeg isocyanate and GC isocyanate and lubricity changes.

|  | Date | Lot |  | MW | Vic | Insertion | Withdrawal |
|---|---|---|---|---|---|---|---|
| HA Supplier A ARM | Mar. 29, 2011 | 12424 | NO MODIFICATION | 2.59 M | 1448-1514 | 15.412 | 39.108 |
| HA Supplier A NO ARM | Mar. 29, 2011 | 12424 | NO MODIFICATION | 2.59 M | 1448-1514 | 17.178 | 40.154 |
| HA Supplier A ARM | Mar. 29, 2011 | 16066 | NO MODIFICATION | 741,000 | 78.2-83.6@ | 10.879 | 19.124 |
| HA Supplier A NO ARM | Mar. 29, 2011 | 23588 | NO MODIFICATION | 1.60 M | 513-544 | 20.86 | 43.654 |
| HA Supplier A ARM | Mar. 29, 2011 | 23588 | NO MODIFICATION | 1.50 M | 513-544 | 19.127 | 32.92 |
| HA Supplier B ARM | Mar. 29, 2011 |  | NO MODIFICATION | 2.0 M | 831-861 | 21.298 | 36.243 |
| HA Supplier B NO ARM | Mar. 29, 2011 |  | NO MODIFICATION | 2.0 M | 831-861 | 20.653 | 37.592 |
| HA Supplier A ARM | Mar. 30, 2011 | 16066 | MODIFIED | 741,000 | 82-90@12 F. | 13.723 | 18.567 |
| HA Supplier A NO ARM | Mar. 30, 2011 | 16066 | MODIFIED | 741,000 | 82-90@12 F. | 13.82 | 17.261 |
| HA Supplier A NO ARM | Mar. 30, 2011 | 23588 | MODIFIED | 1.60 M | 82-90@12 F. | 12.727 | 15.926 |
| HA Supplier A ARM | Mar. 30, 2011 | 23588 | MODIFIED | 1.60 M | 82-90@12 F. | 10.848 | 13.793 |
| HA Supplier A NO ARM | Mar. 30, 2011 | 12424 | MODIFIED | 2.59 M | 1494-1526 | 15.461 | 20.028 |
| HA Supplier A ARM | Mar. 30, 2011 | 12424 | MODIFIED | 2.59 M | 1494-1526 | 15.86 | 18.292 |
| HA Supplier B NO ARM | Mar. 30, 2011 |  | MODIFIED | 2.0 M | 690-710 3.0 | 14.098 | 16.351 |
| HA Supplier B ARM | Mar. 30, 2011 |  | MODIFIED | 2.0 M | 690-710 3.0 | 12.014 | 15.96 |

The above insertion and withdrawal forces measurements (in grams) were taken using an Instron® tester using the same insertion and withdrawal procedure for each measurement. The guidewire on which the respective dip-coated compositions were placed had a tungsten loaded polyurethane jacket on which a base coat of concurrently filed application titled Oxirane (Ethylene Oxide) Polyurethane Coatings, U.S. Pat. No. 9,255,173 to Edwards, which is incorporated by reference herein, had been deposited. Compositions of the present invention were then dip coated onto the base coat of the guidewire.

EXAMPLE 4

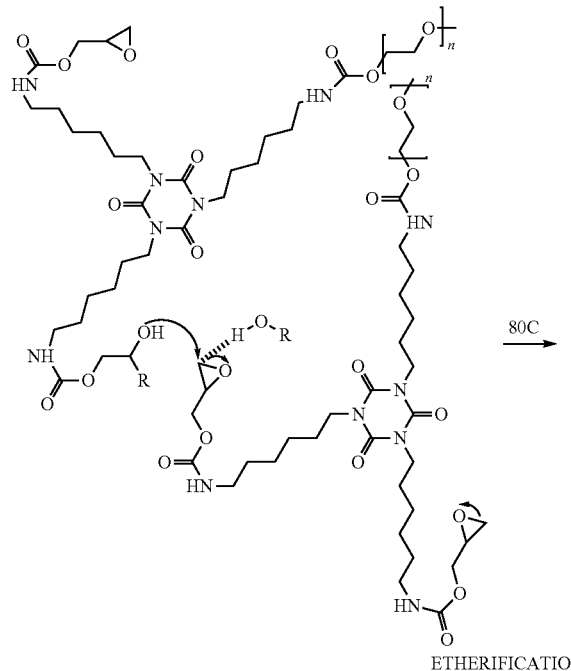

R = Neucleophile

ETHERIFICATION a. (Fully Modified Mpeg/GC-Carbamate HA)
To a four ounce bottle 1.0 grams of mpeg/GC-carbamate were added to 3.0 grams Hyaluronan. The bottle was then placed into a 80 C for 2.0 hours. The contents were then added to a 32 ounce bottle and filled with 700 grams distilled water. The material formed a hydrogel that was dissolved in water by mixing at 500 RPMs for 2-3 hours.

b. (Partially Modified HA)
To a four ounce bottle 0.005 grams of mpeg/GC-carbamate were added to 3.0 grams Hyaluronan. The bottle was then placed into an 80 C oven for 2.0 hours. The contents were then added to a 32 ounce bottle and filled with 700 grams distilled water. The material formed a hydrogel that was dissolved in water by mixing at 500 RPMs for 2-3 hours.

c. (Fully Modified Mpeg/GC-Carbamate HA)
To a four ounce bottle 1.0 grams of mpeg/GC-carbamate were added to 3.0 grams Hyaluronan. The bottle was then placed into a 40 C oven overnight. The contents were then added to a 32 ounce bottle and filled with 700 grams distilled water. The material formed a hydrogel that was dissolved in water by mixing at 500 RPMs for 2-3 hours.

d. (Partially Modified HA)
To a four ounce bottle 0.005 grams of mpeg/GC-carbamate were added to 3.0 grams Hyaluronan. The bottle was then placed into an 80 C oven for two hours. The contents were then added to a 32 ounce bottle and filled with 700 grams distilled water. The material formed a hydrogel that was dissolved in water by mixing at 500 RPMs for 2-3 hours.

FTIR measurements were performed using a Shimadzu IRAffinity-1 with a MIRacle single-bounce ATR accessory using IRsolution software. Spectra acquisitions were based on 100 scans. The FTIR was set for auto gain to monitor spectral ranges of 4000 cm$^{-1}$ to 700 cm$^{-1}$.

Monitoring of the epoxide band (910 cm$^{-1}$) was used to determine reactions with hydroxyl functionality or the self-crosslinking reactions that may occur by nucleophilic attack. The disappearance of the epoxide absorbance band is a result of reaction completion. When presented and heated with hydroxyl functionality, from Hyaluronan, or alone the reaction proceeds to completion shows that molecular weight remains similar to unmodified Hyaluronan due to the system being slightly crosslinked.

EXAMPLE 5

Higher amounts of '956 patent material modifier added to HA, then heated to 8.degree. C. for 2 hrs, yield better lubricity and durability (Table 1.0). Notice withdrawal results for HA 30 are much lower than for HA 28 and HA 29. Withdrawal results correspond most to physician feel.

| | Patent Material | Amt. HA | Amt. '956 INS | WD | INS | WD |
|---|---|---|---|---|---|---|
| HA 30 coated at 0.15/4.5 | 2.5 g | 700 g | 9.877 | 10.486 | 12.067 | 11.785 |
| HA 29 coated at 0.15/4.5 | 1.0 g | 700 g | 10.968 | 12.165 | 15.537 | 14.019 |
| HA 28 coated at 0.15/4.5 | 0.0 g | 700 g | 10.399 | 10.594 | 16.211 | 15.86 |

EXAMPLE 6

Use of Adhesion Promoter on a Bare Metal Substrate
  Step 1: Preparation of Adhesion Promoter
1. 100 mL ETOH (ETOH anhydrous)
2. Add 5.0 gram water
3. Stir 10 minutes
4. Add 3.84 grams amino-silane
  I. Examples of amino-silane are:
    1. 3-aminopropyltriethoxysilane (Provided by Gelest)
    2. 3-aminoethyltriethoxysilane (Provided by Gelest)
    3. 3-trimethoxysilylpropyl-diethylenetriamine (Provided by Gelest)
5. Mix 5 minutes
  Step 2: Coating Wire Bare Metal Substrate with Adhesion Promoter
1. Pour adhesion promoter into 100 mL burette (use shaker to mix)
2. Place wire in graduated cylinder solution for 10 minutes
3. Take wire out of solution and place in 125 C oven for 10 minutes

What is claimed is:

1. An HA-based composition, comprising the reaction product of:
  a) an HA-compound selected from the group consisting of a hyaluronic acid, a hyaluronate, a hyaluronan, and salts thereof; and
  b) a water dispersible epoxy urethane (glycidyl carbamate) of formula I or II, or a self-crosslinked derivative thereof:

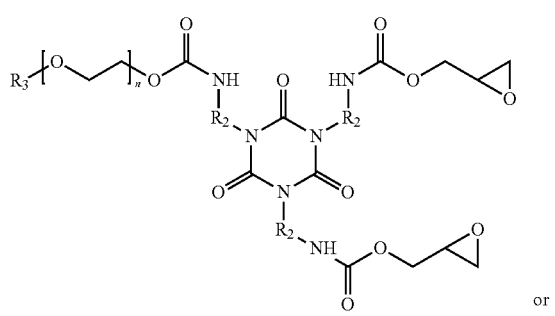

(I)

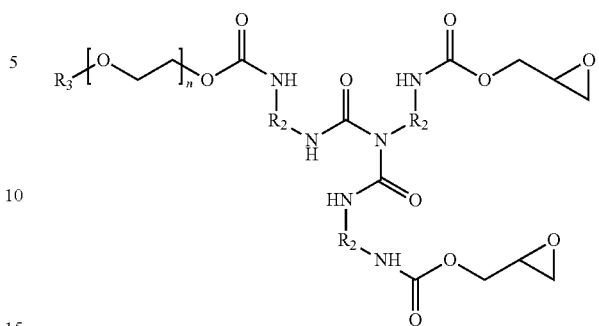

(II)

wherein:
  i) n ranges from 1 to 50;
  ii) $R_2$ is independently an optionally substituted divalent $C_1$-$C_{15}$ alkyl, an optionally substituted divalent $C_{13}$-$C_{15}$ cycloalkyl, or a group selected from:

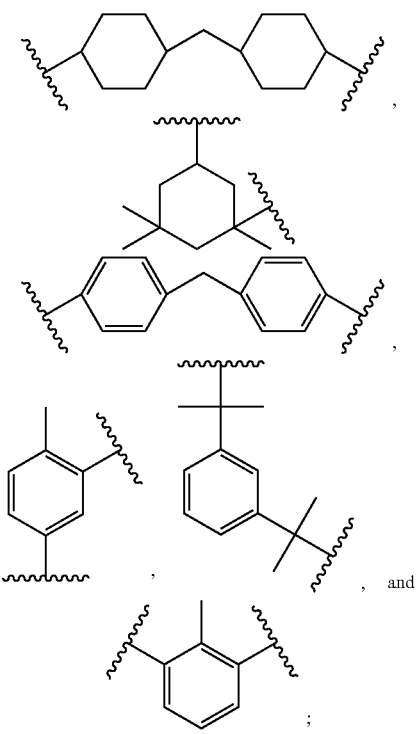

and
  iii) $R_3$ is independently an optionally substituted $C_1$-$C_{15}$ alkyl.

2. The HA-based composition of claim 1 wherein the water dispersible epoxy urethane (glycidyl carbamate) is of formula I.

3. The HA-based composition of claim 2 wherein n=1, $R_2$=(—$CH_2$—)$_6$ as a divalent hexamethylene alkyl, and $R_3$ is independently an optionally substituted $C_1$-$C_{15}$ alkyl.

4. The HA-based composition of claim 2 in which the glycidyl carbamate moiety is self-cross-linked.

5. The HA-based composition of claim 1 having a molecular weight in the range of about 10,000 to about 8,000,000.

6. A method of coating a substrate with a water dispersible coating composition, comprising the step of applying the HA-based composition of claim 1 to a substrate.

7. The method of claim 6 including selecting the substrate from the group consisting of plastic and metal.

8. An HA-based composition, comprising the reaction product of:
   a) an HA-compound selected from the group consisting of a hyaluronic acid, a hyaluronate, a hyaluronan, and salts thereof coupled to polyalkylene glycol end-capped isocyanate; and
   b) a water dispersible epoxy urethane (glycidyl carbamate) of formula I or II:

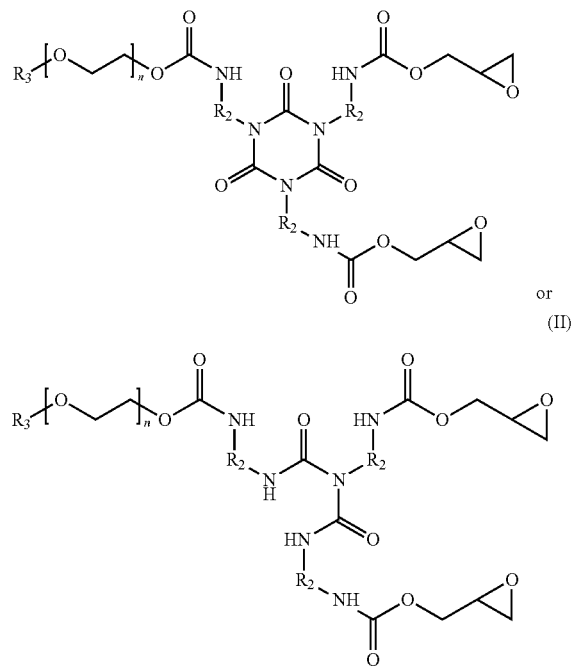

c) wherein:
   i) n ranges from 1 to 50;
   ii) $R_2$ is independently an optionally substituted divalent $C_1$-$C_{15}$ alkyl, an optionally substituted divalent $C_3$-$C_{15}$ cycloalkyl, or a group selected from:

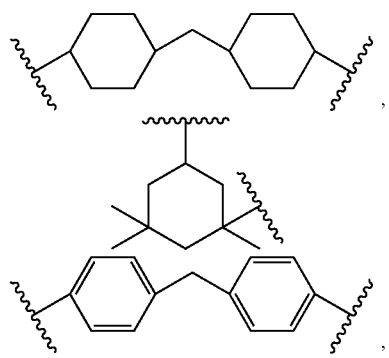

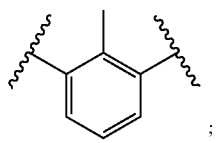

and iii) $R_3$ is independently an optionally substituted $C_1$-$C_{15}$ alkyl.

9. The HA-based composition of claim 8 wherein the water dispersible epoxy urethane (glycidyl carbamate) is of formula (I).

10. The HA-based composition of claim 9 wherein:
    a) n=1, $R_2$=(—$CH_2$—)$_6$ as a divalent hexamethylene alkyl, and
    b) $R_3$ is independently an optionally substituted $C_1$-$C_{15}$ alkyl.

11. The HA-based composition of claim 8 having a molecular weight in the range of about 10,000 to about 8,000,000.

12. The HA-based composition of claim 8, wherein the glycidyl carbamate moiety reacts with hydroxyl functionality of the HA-compound.

13. The HA-based composition of claim 8, wherein the glycidyl carbamate moiety reacts with carboxylic acid functionality of the HA-compound.

14. The HA-based composition of claim 8, as a mixture of from 0.01% to 99.99% of the HA-based composition having an mPEG end-cap, the remainder being glycidyl end capped isocyanate mixed pre-polymer.

15. A method of coating a substrate with a water dispersible coating composition, comprising the step of applying the HA-based composition of claim 8 to a substrate.

16. The method of claim 15 including selecting the substrate from the group consisting of plastic and metal.

17. An HA-based composition, consisting essentially of the reaction product of:
    a) an HA-compound selected from the group consisting of a hyaluronic acid, a hyaluronate, a hyaluronan, and salts thereof; and
    b) a water dispersible epoxy urethane (glycidyl carbamate) of formula I or II, or a self-crosslinked derivative thereof:

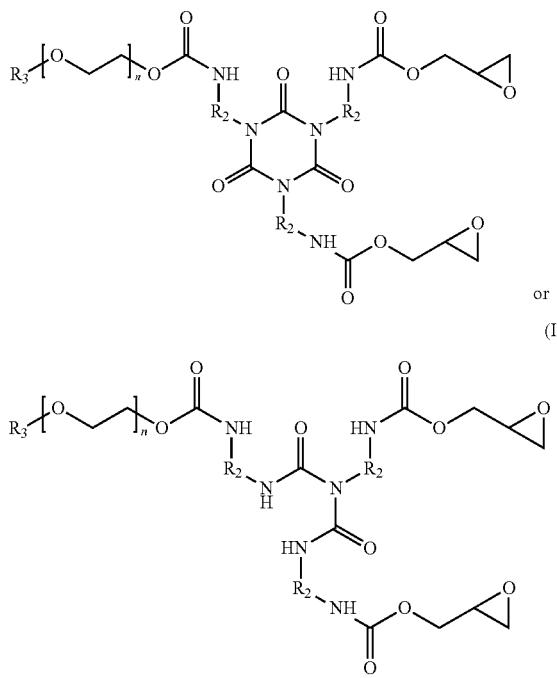

(I)

or (II)

wherein:
i) n ranges from 1 to 50;
ii) R$_2$ is independently an optionally substituted divalent C$_1$-C$_{15}$ alkyl, an optionally substituted divalent C$_{13}$-C$_{15}$ cycloalkyl, or a group selected from:

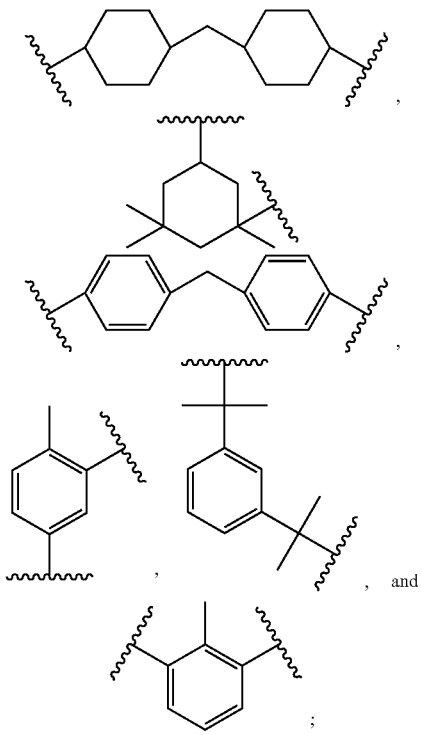

;

and
iii) R$_3$ is independently an optionally substituted C$_1$-C$_{15}$ alkyl.

18. The HA-based composition of claim 17 wherein the water dispersible epoxy urethane (glycidyl carbamate) is of formula I.

19. The HA-based composition of claim 18 wherein n=1, R$_2$=(—CH$_2$—)$_6$ as a divalent hexamethylene alkyl, and R$_3$ is independently an optionally substituted C$_1$-C$_{15}$ alkyl.

20. The HA-based composition of claim 18 in which the glycidyl carbamate moiety is self-cross-linked.

21. The HA-based composition of claim 17 having a molecular weight in the range of about 10,000 to about 8,000,000.

22. An HA-based composition, consisting essentially of the reaction product of:
  a) an HA-compound selected from the group consisting of a hyaluronic acid, a hyaluronate, a hyaluronan, and salts thereof coupled to polyalkylene glycol end-capped isocyanate; and
  b) a water dispersible epoxy urethane (glycidyl carbamate) of formula I or II:

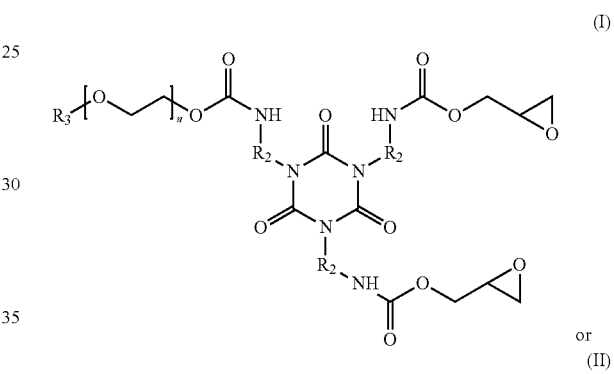

(I)

or

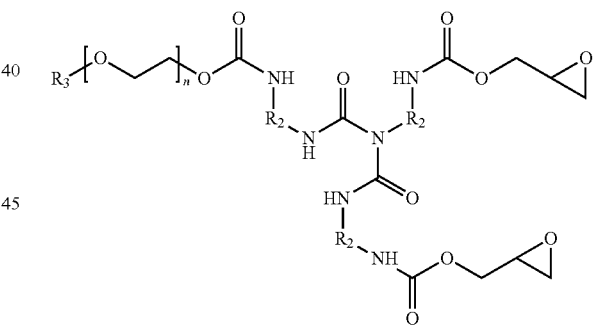

(II)

c) wherein:
  i) n ranges from 1 to 50;
  ii) R$_2$ is independently an optionally substituted divalent C$_1$-C$_{15}$ alkyl, an optionally substituted divalent C$_3$-C$_{15}$ cycloalkyl, or a group selected from:

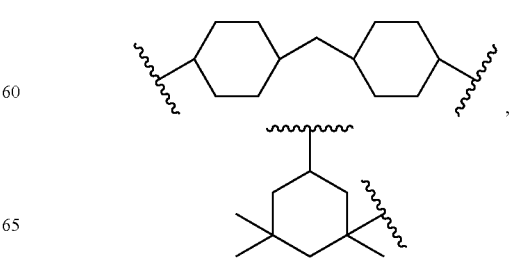

-continued

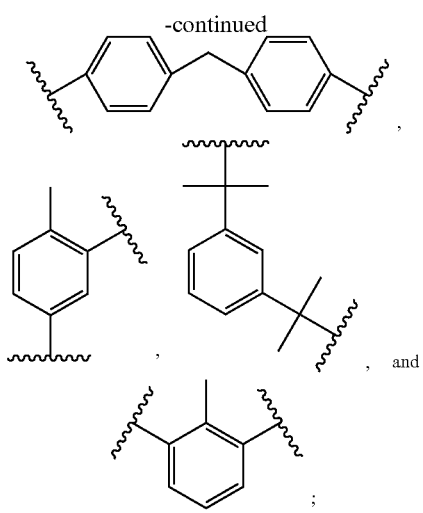

and iii) $R_3$ is independently an optionally substituted $C_1$-$C_{15}$ alkyl.

23. The HA-based composition of claim 22 wherein the water dispersible epoxy urethane (glycidyl carbamate) is of formula (I).

24. The HA-based composition of claim 23 wherein:
a) n=1, $R_2$=(—$CH_2$—)$_6$ as a divalent hexamethylene alkyl, and
b) $R_3$ is independently an optionally substituted $C_1$-$C_{15}$ alkyl.

25. The HA-based composition of claim 22 having a molecular weight in the range of about 10,000 to about 8,000,000.

26. The HA-based composition of claim 22, wherein the glycidyl carbamate moiety reacts with hydroxyl functionality of the HA-compound.

27. The HA-based composition of claim 22, wherein the glycidyl carbamate moiety reacts with carboxylic acid functionality of the HA-compound.

28. The HA-based composition of claim 22, as a mixture of from 0.01% to 99.99% of the HA-based composition having an mPEG end-cap, the remainder being glycidyl end capped isocyanate mixed pre-polymer.

* * * * *

UNITED STATES PATENT AND TRADEMARK OFFICE
CERTIFICATE OF CORRECTION

PATENT NO. : 9,623,157 B2  
APPLICATION NO. : 15/231844  
DATED : April 18, 2017  
INVENTOR(S) : Peter Anthony Edwards Page 1 of 1

It is certified that error appears in the above-identified patent and that said Letters Patent is hereby corrected as shown below:

In the Claims

Column 15, Line 51 (Claim 8 c) ii), delete "$C_3$-$C_{15}$" and insert --$C_{13}$-$C_{15}$--

Signed and Sealed this  
Twentieth Day of June, 2017

Joseph Matal  
*Performing the Functions and Duties of the*  
*Under Secretary of Commerce for Intellectual Property and*  
*Director of the United States Patent and Trademark Office*